United States Patent [19]

Nakayama et al.

[11] 4,280,958
[45] Jul. 28, 1981

[54] PROCESS FOR PRODUCING INDOLINE DERIVATIVE

[75] Inventors: Yoshiki Nakayama, Shimizu; Yasushi Higuchi, Shizuoka; Chihiro Yazawa, Yokohama, all of Japan

[73] Assignee: Ihara Chemical Industry Co., Ltd., Tokyo, Japan

[21] Appl. No.: 81,487

[22] Filed: Oct. 3, 1979

[30] Foreign Application Priority Data

Oct. 31, 1978 [JP] Japan ................... 53-134309

[51] Int. Cl.³ .......................... C07D 209/08
[52] U.S. Cl. .......................... 260/326.11 R
[58] Field of Search ................ 260/326.11 R

[56] References Cited

U.S. PATENT DOCUMENTS

| | | | |
|---|---|---|---|
| 4,087,442 | 5/1978 | Nakayama et al. | 260/326.11 R |
| 4,159,271 | 6/1979 | Sano et al. | 260/326.11 R |

OTHER PUBLICATIONS

W. Houlihan (ed.), *Indoles*, Part One, pp. 464-465, Wiley-Interscience, N.Y., (1972).
R. Sundberg, *The Chem. of Indoles*, p. 197, Academic Press, N.Y., (1970).
R. Morrison, et al., *Org. Chem.* pp. 740, 743-744, Allyn & Bacon, Boston, (1967).

*Primary Examiner*—Donald G. Daus
*Assistant Examiner*—M. C. Eakin
*Attorney, Agent, or Firm*—Oblon, Fisher, Spivak, McClelland & Maier

[57] ABSTRACT

An indoline derivative having the formula

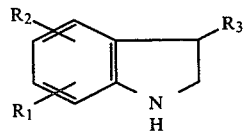

is produced by a cyclization of 2-halogenophenethylamine having the formula

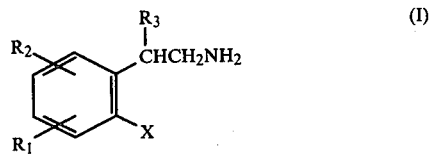

wherein $R_1$ represents a hydrogen atom or a lower alkyl, a lower alkoxyl, nitro or hydroxyl group; $R_2$ represents a hydrogen atom or a lower alkoxyl or nitro group; and $R_3$ represents a hydrogen atom, a lower alkyl, a substituted lower alkyl or a substituted amino group; and X represents a halogen atom in the presence of a copper type catalyst and an amine which is selected from the group consisting of (1) compounds having the formula $R_{3-n}NH_n$ wherein R represents a $C_{1-16}$ alkyl group or $C_{1-8}$ alkoxy group; n is 0 to 2 and R can be the same or different in the case of n is 1 or 0; (2) compounds having the formula $H_2N(CH_2)_nNH$ and $H_2N(CH_2)_nNH(CH_2)_nNH_2$ wherein n is an integer of 2 to 6; (3) compounds having the formula

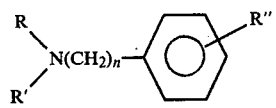

wherein R and R' are the same or different and respectively hydrogen atom, a $C_{1-4}$ alkyl group; n is 0 to 2; and R" represents a hydrogen atom, a halogen atom, a $C_{1-4}$ alkyl group or a $C_{1-4}$ alkoxy group; and (4) compounds having the formula

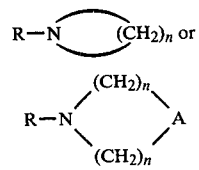

wherein R represents a hydrogen atom, a $C_{1-4}$ alkyl group; A represents O or NH; n is 2 to 5.

3 Claims, No Drawings

PROCESS FOR PRODUCING INDOLINE DERIVATIVE

BACKGROUND OF THE INVENTION

1. Field of the Invention

The present invention relates to a process for producing an indoline derivative having high purity in high yield.

2. Description of the Prior Arts

Indoline derivatives are important compounds as intermediates for indoles used as starting materials for agricultural chemicals, medicines, perfumes and dyes. Various processes have been proposed as the process for producing indoline derivatives;

(1) A cyclization of 2-Aminophenethyl alcohol is carried out in the presence of hydrochloric acid (Kagaku Daijiten Vol. 4 page 409 Kyoritsu K.K.) and;

(2) Stannous chloride and conc. hydrochloric acid are added to 2-nitrophenethyl bromide to obtain 2-aminophenethyl bromide and a cyclization of 2-aminophenethyl bromide is carried out to obtain the indolines (J. of the American Chemical Society Vol. 63, page 1563 (1941)).

However, the cyclization of 2-aminophenethyl alcohol in the presence of hydrochloric acid has disadvantages that 2-aminophenethyl alochol is thermally unstable to be easily polymerized to produce a by-product of the polymer. It is difficult to obtain indolines having high purity in high yield.

On the other hand, the process of using 2-nitrophenethyl bromide has a disadvantage of low yield of the object indolines.

The inventors have studied to overcome these conventional disadvantages and have proposed a cyclization of 2-halogenophenethylamines in the presence of a copper catalyst and ammonia (Japanese Unexamined Patent Publication No. 98961/1978). However, in this process, ammonia in a form of gas, liquid or solution is used, and accordingly, it is necessary to carry out the reaction in an autoclave under a pressure of 5 to 35 kg/cm$^2$. Thus, an autoclave is required as a reactor and the reactor should be anticorrosive in view of a by-product as an aqueous solution of ammonium halide. Moreover, the treatment of the wasted water containing ammonium halide is serious problem.

SUMMARY OF THE INVENTION

It is an object of the present invention to overcome said disadvantages.

It is another object of the present invention to produce an indoline derivative having high purity in high yield without a trouble of corrosion of a reactor and a necessity of an autoclave.

The foregoing and other objects of the present invention have been attained by a cyclization of 2-halogenophenethylamine in the presence of a copper type catalyst and an amine.

The present invention is to provide a process for producing an indoline derivative having the formula

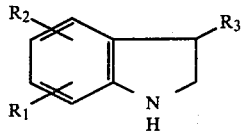

by a cyclization of 2-halogenophenethylamine having the formula

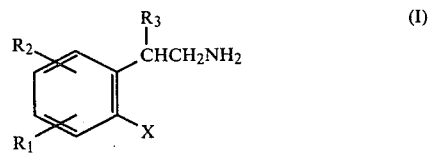

wherein $R_1$ represents a hydrogen atom or a lower alkyl, a lower alkoxyl, nitro or hydroxyl group; $R_2$ represents a hydrogen atom or a lower alkoxyl or nitro group; and $R_3$ represents a hydrogen atom, a lower alkyl, a substituted lower alkyl or a substituted amino group; and X represents a halogen atom in the presence of a copper type catalyst and an amine.

The cyclization of the present invention is shown by the following reaction formula

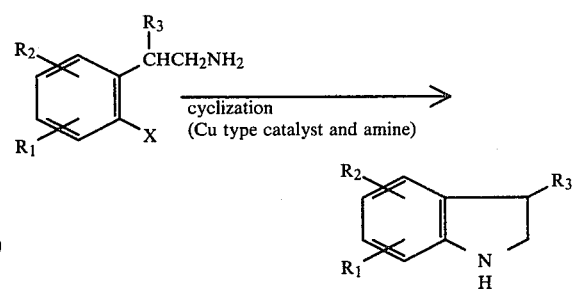

wherein $R_1$, $R_2$, $R_3$ and X are defined above.

In the formula (I), $R_1$ on the benzene ring can be a hydrogen atom; a lower alkyl group such as methyl, ethyl, propyl, isopropyl, butyl and isobutyl group; or a lower alkoxyl group such as methoxy, ethoxy, propoxy and isopropoxy group; nitro group or hydroxyl group, and $R_2$ can be a hydrogen atom; a lower alkoxyl group such as methoxy, ethoxy, propoxy, isopropoxy and butoxy group; or nitro group; and $R_3$ can be a hydrogen atom; a lower alkyl group such as methyl, ethyl, propyl, isopropyl, butyl or isobutyl group; a lower substituted alkyl group or substituting hydrogen atom of the alkyl group by hydroxy, an amino, a nitrile or an alkoxyl group; or a substituted amino group.

In the halogenophenethylamines having the formula (I), X is a halogen atom such as fluorine, chlorine, bromine or iodine atom.

Suitable 2-halogenophenethylamines include 2-chlorophenethylamine, 2-chloro-β-methylphenethylamine, 2-bromo -β-methylphenethylamine, 2-bromo-β-ethylphenethylamine, 2-bromo-β-isopropylphenethylamine, 2-chloro-β-butylphenethylamine, 2-chloro-5-ethylphenethylamine, 2-chloro-5-isopropylphenethylamine, 2-bromo-5-butylphenethylamine, 2-chloro-4-methyl-β-butylphenethylamine, 2-bromo-4-ethyl-β-ethylphenethylamine, 2-bromo-4-isopropyl-5-isopropoxyphenethylamine, 2-chloro-4-methyl-5-isopropoxy-β-methylphenethylamine, 2-fluoro-4-methyl-5-nitrophenethylamine, 2-chloro-4-butyl-5-nitro-β-methylphenethylamine, 2-chloro-4-methoxyphenethylamine, 2-bromo-4-isopropoxyphenethylamine, 2bromo-4-ethoxy-3-ethylphenethylamine, 2-chloro-4,5-dimethoxyphenethylamine, 2-chloro-4,5-diisopropoxy-3-methylphenethylamine, 2-bromo-4-isopropoxy-5-nitrophenethylamine, 2-iodo-4-nitrophenethylamine, 2-chloro-4-nitrophenethylamine, 2-fluoro-4-nitro-β-isopropylphenethylamine, 2-bromo-4-nitro-5-methoxy-β-ethylphenethylamine, 2-bromo-3,5-dinitrophenethylamine, 2-bromo-3,5-dinitro-β-ethylphenethylamine, 2-chloro-4-hydroxyphenethylamine, 2-fluoro-4-hydroxyphenethylamine, 2-chloro-4-hydroxy-3-ethylphenethylamine, 2-chloro-4-hydroxy-5-methoxyphenethylamine, 2-chloro-4-hydroxy-5-isopropoxy-β-isopropylphenethylamine, 2-chloro-4-hydroxy-5-nitrophenethylamine, 2-bromo-4-hydroxy-5-nitro-β-ethylphenethylamine, β-hydroxymethyl-2-chlorophenethylamine, β-aminomethyl-2-chlorophenethylamine, β-N,N-diethylamino-2-chlorophenethylamine, β-(2-N,N-dimethylaminoethyl)-2-chlorophenethylamine, β-cyanomethyl-2-chlorophenethylamine and β-(2,2-diethoxyethyl)-2-chlorophenethylamine, β-(1,3-dioxolan-2-yl)methyl-2-chlorophenethylamine.

The copper type catalysts used in the process of the invention can be a compound which feeds a copper component, such as metallic copper, an inorganic copper compound such as copper chloride, copper bromide, copper iodide, cuprous oxide, cupric oxide, copper hydroxide and copper sulfate; or an organic copper compound such as copper oxalate and copper acetate.

Suitable amines used in the process of the present invention include (1) compounds having the formula

wherein R represents a $C_1$–$C_{16}$ alkyl group or $C_{1-8}$ alkoxy group; n is 0 to 2 and R can be the same or different in the case of n is 1 or 0; such as methylamine, ethylamine, butylamine, hexylamine, pentylamine, octylamine, ethanolamine, propanolamine and butanolamine, dimethylamine, diethylamine, dibutylamine, diethanolamine, dipropanolamine, dibutanolamine, trimethylamine, triethylamine, tripropylamine, tributylamine, triethanolamine, tripropanolamine, tributanolamine, dimethylaminoethanol and diethylaminoethanol; or (2) compounds having the formula

and

wherein n is an integer of 2 to 6; such as ethylenediamine, tetramethylenediamine, hexamethylenediamine, diethylenediamine; (3) compounds having the formula

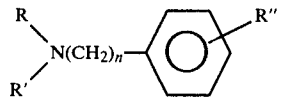

wherein R and R' are the same or different and respectively hydrogen atom, a $C_{1-4}$ alkyl group; n is 0 to 2; and R" represents a hydrogen atom, a halogen atom, a $C_{1-4}$ alkyl group or a $C_{1-4}$ alkoxy group; such as benzylamine, N,N-dimethylbenzylamine, N,N-diethylbenzylamine, p-chloro-N,N-diethylbenzylamine, phenethylamine and o-chloro-phenethylamine; and (4) compounds having the formula

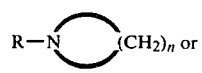

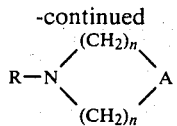

wherein R represents a hydrogen atom, a $C_{1-4}$ alkyl group; A represents O or NH; n is 2 to 5; such as pyridine, piperidine, piperazine, morpholine and N-ethyl morpholine.

Among these amines, it is optimum to use an amine having a boiling point of higher than 100° C. in order to carry out the reaction under the atmospheric pressure.

When 2-halogenophenethylamine having the formula (I) wherein $R_1$ or $R_2$ is nitro group, it is preferable to use a tertiary amine.

The copper type catalyst is incorporated at a ratio of 0.1 to 20 wt.% preferably 1 to 5 wt.% based on 2-halogenophenethylamine in the process of the present invention.

The amine is incorporated at a molar ratio of more than 1, preferably 2 to 5 based on 2-halogenophenethylamine.

The reaction temperature is higher than 100° C. preferably in a range of 100° to 200° C. The reaction time is preferably in a range of 1 to 6 hours.

The reaction can be carried out under the atmospheric pressure be selecting the amine though the reaction can be carried out under higher pressure by using the amine having a low boiling point.

The reaction is preferably carried out in an inert gas such as nitrogen gas.

In the cyclization, an inert solvent can be incorporated. The inert solvent is preferably an aliphatic hydrocarbon, an aromatic hydrocarbon, a halogenated aliphatic hydrocarbon or a halogenated aromatic hydrocarbon, an ether such as tetrahydrofuran, or an aprotic solvent. It is preferable to use a solvent having a boiling point of higher than 100° C. Excess amine can be used as the solvent.

The solvent can be incorporated so as to dilute the reaction mixture.

In accordance with the process of the present invention, after the reaction, the reaction mixture can be treated by a filtration, a phase separation and a washing with water to obtain a crude indoline derivative. The crude indoline derivative can be purified by the conventional process such as a distillation or a recrystallization to obtain an indoline derivative having high purity.

In accordance with the process of the present invention, the cyclization can be smoothly performed and a formation of a polymerized product can be prevented so that it is superior to the conventional cyclization of 2-aminophenethylalcohol in the presence of hydrochloric acid.

In accordance with the process of the present invention, the cyclization can be carried out under the atmospheric pressure or lower pressure and an autoclave requiring complicated operations need not be used so that it is superior to the conventional cyclization of 2-halogenophenylthylamine in the presence of ammonia. In accordance with the process of the present invention, the indoline derivative having high purity can be obtained in high yield.

The present invention will be further illustrated by certain examples and references which are provided for purposes of illustration only and are not intended to be limiting the present invention.

EXAMPLE 1

In a 100 ml. flask equipped with a condenser, a thermometer, a stirrer and a dropping funnel, 21.8 g. of ethanolamine was charged and stirred at room temperature in nitrogen gas atmosphere, and 1.56 g. of anhydrous cupric chloride was gradually added to it. Exothermic reaction was resulted. Then, the mixture was heated at 150° C. with stirring in the nitrogen gas flow and 15.56 g. of 2-chlorophenethylamine was added dropwise and the mixture was stirred for 3 hours to complete the reaction. Then, 30 ml. of xylene was added dropwise and the mixture was refluxed for 10 minutes with stirring. The reaction mixture was cooled to a room temperature and xyleneindoline layer was washed with 20 ml. of water and concentrated under a reduced pressure to obtain 11.1 g. of indoline having a purity of 99.9%. The yield was 93.0%.

EXAMPLES 2 to 11

In accordance with the process of Example 1, except using various amines shown in Table 1 instead of ethanolamine, each indoline was produced. The results are shown in Table 1.

TABLE 1

| | | Condition of reaction | | Indoline | |
|---|---|---|---|---|---|
| Exp. | Amine | Temp. (°C.) | Time (hr) | Purity (%) | Yield (%) |
| 2 | hexylamine | 130 | 10 | 99.9 | 93 |
| 3 | octylamine | 150 | 3 | " | 95 |
| 4 | dibutylamine | " | " | " | 94 |
| 5 | tripropylamine | " | " | " | 93 |
| 6 | tetramethyleneamine | " | " | " | 92 |
| 7 | diethylaminoethanol | " | " | " | 93 |
| 8 | benzylamine | " | " | " | 92 |
| 9 | phenethylamine | " | " | 99.6 | 94 |
| 10 | piperazine | 145 | 4 | 99.9 | 92 |
| 11 | morpholine | 128 | 15 | " | 91 |

EXAMPLES 12 to 24

In accordance with the process of Example 1 except using various amines instead of ethanolamine, and various 2-halogenophenethylamine (0.1 mole), each indoline derivative was produced. The conditions and components in the reaction are shown in Table 2.

REFERENCE 1

In a 200 ml. of ethanol, 46 g. of 2-nitrophenethyl bromide was dissolved and a mixture of 181 1 g. of stannous chloride hydrate and 168 ml. of conc. hydrochloric acid in 100 ml. of water was heated to 60° C. and added to the former mixture. The reaction was carried out. After the reaction, the reaction mixture was cooled to be lower than 10° to 20° C. and a cold solution of 400 g. of sodium hydroxide in 500 L ml. of water was added. Then, the product was extracted with ether and ether was distilled off. A cyclization of the resulting o-aminophenethyl bromide was carried out at 150° C. After the reaction, the reaction mixture was cooled and 20% aqueous solution of sodium hydroxide was added to be an alkaline condition. The resulting oily product was extracted with ether and ether was distilled off to obtain 14 g. of indoline having a purity of 98.6% in a yield of 58.0%.

REFERENCE 2

In a 300 ml. autoclave, 15.6 g. of 2-chlorophenethylamine, 72.9 g. of 14% ammonium aqueous solution and 0.47 g. of cuprous chloride were charged. The autoclave was purged with nitrogen gas, and the reaction was carried out at 150° C. for 2 hours with stirring. The pressure in the autoclave was cooled to the room temperature after the reaction and 100 ml. of benzene was added to the reaction mixture and an organic layer was separated and washed with water and benzene was distilled off under a reduced pressure. The residue was distilled to obtain 11.3 g. of indoline having a purity of 95.6% in a yield of 90.8%.

TABLE 2

| | | | Condition of reaction | | | | |
|---|---|---|---|---|---|---|---|
| Exp. | 2-Halogenophenethyl-amine | Amines | Temp. (°C.) | Time (hr) | Indoline derivative | Purity (%) | Yield (%) |
| 12 | 2-chloro-β-methyl-phenethylamine | monoethanol-amine | 150 | 3 | 3-methylindoline | 99.9 | 94 |
| 13 | 2-bromo-β-ethyl-phenethylamine | octylamine | " | " | 3-ethylindoline | 99.9 | 94 |
| 14 | 2-chloro-β-butyl-phenethylamine | dibutylamine | " | " | 3-butylindoline | 99.9 | 94 |
| 15 | 2-chloro-5-isopropyl-phenethylamine | tributylamine | " | " | 5-isopropylindoline | 99.9 | 94 |
| 16 | 2-chloro-4-methyl-β-butylphenethyl-amine | diethylene-triamine | " | " | 3-butyl-6-methylindoline | 99.9 | 94 |
| 17 | 2-bromo-4-isopropoxy phenethylamine | diethanol-amine | 120 | " | 6-isopropyl-5-isopropoxyindoline | 99.9 | 95 |
| 18 | 2-chloro-4-methoxy-phenethylamine | diethylamino-ethanol | 150 | " | 6-methoxyindoline | 99.9 | 94 |
| 19 | 2-chloro-4,5-diisopropoxy-β-methylphenethylamine | N,N-dimethyl-benzylamine | " | " | 3-methyl-5,6-diisopropoxyindoline | 99.9 | 94 |
| 20 | 2-chloro-5-nitro-phenethylamine | triethylamine | 80 | " | 5-nitroindoline | 99.9 | 90 |
| 21 | 2-fluoro-4-hydroxy-phenethylamine | piperidine | 100 | " | 6-hydroxyindoline | 99.9 | 95 |
| 22 | 2-chloro-4-hydroxy-5-methoxyphenethyl-amine | piperazine | 150 | " | 5-methoxy-6-hydroxyindoline | 99.9 | 94 |
| 23 | β-(2,2-diethoxy- | | | | 3-(2-diethoxyethyl)indoline | 99.9 | 94 |

TABLE 2-continued

| Exp. | 2-Halogenophenethyl-amine | Amines | Condition of reaction Temp. (°C) | Time (hr) | Indoline derivative | Purity (%) | Yield (%) |
|---|---|---|---|---|---|---|---|
|  | ethyl)-2-chloro-phenethylamine | monoethanol-amine | " | " |  |  |  |
| 24 | β-(1,3-dioxolan-2-yl)-methyl-2-chloro-phenethylamine | monoethanol-amine | " | " | 3-(1,3-dioxolan-2-yl-methyl)indoline | 99.9 | 94 |
| Ref 1 | 2-nitrophenethyl-bromide | SnCl$_2$ + Conc. HCl | 60 | — | indoline | 98.6 | 58 |
| Ref 2 | 2-chlorophenethyl-amine | 14% ammonium aqueous solution | 150 (13 kg/cm$^2$) | 2 | indoline | 95.6 | 90.8 |

We claim:

1. A process for producing an indoline derivative having the formula

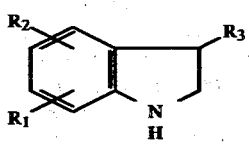

by a cyclization of 2-halogenophenethylamine having the formula

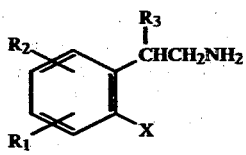 (I)

wherein $R_1$ represents a hydrogen atom or a lower alkyl, a lower alkoxyl, nitro or hydroxyl group; $R_2$ represents a hydrogen atom or a lower alkoxyl or nitro group; and $R_3$ represents a hydrogen atom, a lower alkyl, hydroxy lower alkyl, amino lower alkyl, nitrilo lower alkyl, lower alkoxyl lower alkyl, or lower alkyl-amino group; and X represents a halogen atom in the presence of a copper type catalyst which supplies copper ions, and an amine selected from the group consisting of (1) compounds having the formula $$R_{3-n}NH_n$$

wherein R represents a $C_{1-16}$ alkyl group or $C_{1-8}$ alkoxy group; n is 0 to 2 and R can be the same or different in the case of n is 1 or 0; (2) compounds having the formula $$H_2N(CH_2)_nNH_2 \text{ and}$$

$$H_2N(CH_2)_nNH(CH_2)_nNH_2$$

wherein n is an integer of 2 to 6; (3) compounds having the formula

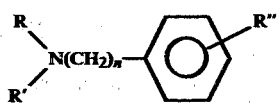

wherein R and R' are the same or different and respectively hydrogen atom, a $C_{1-4}$ alkyl group; n is 0 to 2; and R" represents a hydrogen atom, a halogen atom, a $C_{1-4}$ alkyl group or a $C_{1-4}$ alkoxy group; and (4) compounds having the formula

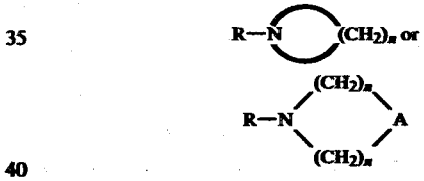

wherein R represents a hydrogen atom, a $C_{1-4}$ alkyl group; A represents O or NH; n is 2 to 5.

2. A process according to claim 1 wherein the amine is incorporated at a molar ratio of more than 1 based on the 2-halogenophenethylamine.

3. A process according to claim 1 wherein the copper type catalyst is metallic copper, an inorganic copper compound or an organic copper compound and is incorporated at a ratio of 0.1 to 20 wt. % based on the 2-halogenophenethylamine.

* * * * *